US010221258B2

(12) United States Patent
Yang et al.

(10) Patent No.: US 10,221,258 B2
(45) Date of Patent: Mar. 5, 2019

(54) METHODS FOR RESTORING METALLOCENE SOLIDS EXPOSED TO AIR

(71) Applicant: Chevron Phillips Chemical Company LP, The Woodlands, TX (US)

(72) Inventors: Qing Yang, Bartlesville, OK (US); Tony R. Crain, Niotaze, KS (US); George R. Rajaendran, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 63 days.

(21) Appl. No.: 15/461,523

(22) Filed: Mar. 17, 2017

(65) Prior Publication Data

US 2018/0265606 A1   Sep. 20, 2018

(51) Int. Cl.
 C07F 17/00 (2006.01)
 C08F 4/6592 (2006.01)
 C08F 10/02 (2006.01)
 C08F 4/6392 (2006.01)

(52) U.S. Cl.
 CPC .............. C08F 10/02 (2013.01); C07F 17/00 (2013.01); C08F 4/63925 (2013.01); C08F 4/6592 (2013.01); C08F 2420/01 (2013.01)

(58) Field of Classification Search
 CPC ........................ C07F 17/00; C08F 4/6592
 See application file for complete search history.

(56) References Cited

U.S. PATENT DOCUMENTS

| | | |
|---|---|---|
| 3,242,099 A | 3/1966 | Manyik et al. |
| 3,248,179 A | 4/1966 | Norwood |
| 4,501,885 A | 2/1985 | Sherk et al. |
| 4,588,790 A | 5/1986 | Jenkins, III et al. |
| 4,794,096 A | 12/1988 | Ewen |
| 4,808,561 A | 2/1989 | Welborn, Jr. |
| 5,352,749 A | 10/1994 | Sher |
| 5,436,304 A | 7/1995 | Griffin et al. |
| 5,565,175 A | 10/1996 | Hottovy et al. |
| 5,575,979 A | 11/1996 | Hanson |
| 5,576,259 A | 11/1996 | Hasegawa et al. |
| 5,807,938 A | 9/1998 | Kaneko et al. |
| 5,919,983 A | 7/1999 | Rosen et al. |
| 6,107,230 A | 8/2000 | McDaniel et al. |
| 6,165,929 A | 12/2000 | McDaniel et al. |
| 6,239,235 B1 | 5/2001 | Hottovy et al. |
| 6,262,191 B1 | 7/2001 | Hottovy et al. |
| 6,294,494 B1 | 9/2001 | McDaniel et al. |
| 6,300,271 B1 | 10/2001 | McDaniel et al. |
| 6,316,553 B1 | 11/2001 | McDaniel et al. |
| 6,355,594 B1 | 3/2002 | McDaniel et al. |
| 6,376,415 B1 | 4/2002 | McDaniel et al. |
| 6,388,017 B1 | 5/2002 | McDaniel et al. |
| 6,391,816 B1 | 5/2002 | McDaniel et al. |
| 6,395,666 B1 | 5/2002 | McDaniel et al. |
| 6,524,987 B1 | 2/2003 | Collins et al. |
| 6,548,441 B1 | 4/2003 | McDaniel et al. |
| 6,548,442 B1 | 4/2003 | McDaniel et al. |
| 6,576,583 B1 | 6/2003 | McDaniel et al. |
| 6,613,712 B1 | 9/2003 | McDaniel et al. |
| 6,632,894 B1 | 10/2003 | McDaniel et al. |
| 6,667,274 B1 | 12/2003 | Hawley et al. |
| 6,750,302 B1 | 6/2004 | McDaniel et al. |
| 6,833,415 B2 | 12/2004 | Kendrick et al. |
| 7,026,494 B1 | 4/2006 | Yang et al. |
| 7,041,617 B2 | 5/2006 | Jensen et al. |
| 7,199,073 B2 | 4/2007 | Martin et al. |
| 7,226,886 B2 | 6/2007 | Jayaratne et al. |
| 7,294,599 B2 | 11/2007 | Jensen et al. |
| 7,312,283 B2 | 12/2007 | Martin et al. |
| 7,517,939 B2 | 4/2009 | Yang et al. |
| 7,531,606 B2 | 5/2009 | Hendrickson |
| 7,598,327 B2 | 10/2009 | Shaw |
| 7,601,665 B2 | 10/2009 | McDaniel et al. |
| 7,619,047 B2 | 11/2009 | Yang et al. |
| 7,884,163 B2 | 2/2011 | McDaniel et al. |
| 7,919,639 B2 | 4/2011 | Murray et al. |
| 8,080,681 B2 | 12/2011 | Murray et al. |
| 8,114,946 B2 | 2/2012 | Yang et al. |
| 8,309,485 B2 | 11/2012 | Yang et al. |
| 8,623,973 B1 | 1/2014 | McDaniel et al. |
| 8,703,886 B1 | 4/2014 | Yang et al. |
| 8,822,608 B1 | 9/2014 | Bhandarkar et al. |
| 9,023,959 B2 | 5/2015 | McDaniel et al. |
| 9,163,098 B2 | 10/2015 | McDaniel et al. |
| 9,303,106 B1 | 4/2016 | Clark et al. |
| 9,481,749 B1 | 11/2016 | Clark et al. |
| 9,493,592 B2 | 11/2016 | Cymbaluk et al. |
| 9,598,515 B2 | 3/2017 | Clark et al. |

FOREIGN PATENT DOCUMENTS

WO   WO 97/21717   6/1997

OTHER PUBLICATIONS

International Search Report and the Written Opinion of the International Searching Authority in PCT/US2018/021027 dated May 28, 2018, 11 pages.
Vieyra-Eusebio et al., entitled "Vapor Pressures and Sublimation Enthalpies of Nickelocene and Cobaltocene Measured by Thermogravimetry," Journal of Chemical and Engineering Data, vol. 56, 2011, pp. 5008-5018.
Eilertsen et al., entitled "Activation of Metallocenes for Olefin Polymerization as Monitored by IR Spectroscopy," Inorganic Chemistry, vol. 44, No. 13, 2005, pp. 4843-4851.
*Film Extrusion Manual—Process, Materials, Properties*, TAPPI Press, 1992, 16 pages.
*Modern Plastics Encyclopedia*, Mid-Nov. 1995 Issue, vol. 72, No. 12, 3 pages.

*Primary Examiner* — Caixia Lu
(74) *Attorney, Agent, or Firm* — Merchant & Gould P.C.

(57) ABSTRACT

Methods for treating solid metallocene compounds that are exposed to air are disclosed. These methods include a step of contacting the exposed solid metallocene compound with a purging gas stream containing an inert gas, and optionally, subjecting the exposed solid metallocene compound to a sub-atmospheric pressure.

20 Claims, No Drawings

METHODS FOR RESTORING METALLOCENE SOLIDS EXPOSED TO AIR

BACKGROUND OF THE INVENTION

Metallocene compounds, whether in solid form or in solution, are typically stored in an inert gas atmosphere to prevent degradation and loss of catalytic activity. The conventional method to recover metallocene solids that are exposed to air (e.g., oxygen and moisture) is recrystallization, but recrystallization is a specialized and time-consuming process, and is not practical in a production or manufacturing environment. It would be beneficial to have an improved method for recovering metallocene solids that are exposed to air, which does not involve recrystallization. Accordingly, it is to these and other ends that the present disclosure is directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Methods for treating an exposed solid metallocene compound are disclosed and described herein. One such method for treating an exposed solid metallocene compound can comprise (or consist essentially of, or consist of) contacting the exposed solid metallocene compound with a purging gas stream that comprises (or consists essentially of, or consists of) an inert gas, to form a treated solid metallocene compound.

Another method for treating an exposed solid metallocene compound is provided herein, and this method can comprise (or consist essentially of, or consist of), in any order, contacting the exposed solid metallocene compound with a purging gas stream that comprises (or consists essentially of, or consists of) an inert gas, and subjecting the exposed solid metallocene compound to a sub-atmospheric pressure, to form a treated solid metallocene compound.

Beneficially, these methods can result in treated solid metallocene compounds that have comparable color, moisture level, long-term stability, and catalyst activity to that of fresh, unexposed, metallocene compounds that have been stored under nitrogen.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated with or without explicit description of the particular combination. Additionally, unless explicitly recited otherwise, any aspect or feature disclosed herein can be combined to describe inventive designs, compositions, processes, or methods consistent with the present disclosure.

While compositions and methods are described herein in terms of "comprising" various components or steps, the compositions and methods can also "consist essentially of" or "consist of" the various components or steps, unless stated otherwise. For example, a catalyst composition consistent with aspects of the present invention can comprise; alternatively, can consist essentially of; or alternatively, can consist of; a treated solid metallocene compound, an activator, and a co-catalyst.

The terms "a," "an," "the," etc., are intended to include plural alternatives, e.g., at least one, unless otherwise specified. For instance, the disclosure of "an activator-support" or "a metallocene compound" is meant to encompass one, or mixtures or combinations of more than one, activator-support or metallocene compound, respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. A general reference to pentane, for example, includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

The term "polymer" is used herein generically to include olefin homopolymers, copolymers, terpolymers, and so forth, as well as alloys and blends thereof. The term "polymer" also includes all possible geometrical configurations, unless stated otherwise, and such configurations can include isotactic, syndiotactic, and random symmetries. The term "polymer" also includes impact, block, graft, random, and alternating copolymers. A copolymer can be derived from an olefin monomer and one olefin comonomer, while a terpolymer can be derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer can be categorized an as ethylene/1-hexene copolymer. The term "polymer" also is meant to include all molecular weight polymers, and is inclusive of lower molecular weight polymers or oligomers. The term "polymer" as used herein is intended to encompass oligomers derived from any olefin monomer disclosed herein (as well from an olefin monomer and one olefin comonomer, an olefin monomer and two olefin comonomers, and so forth).

In like manner, the scope of the term "polymerization" includes homopolymerization, copolymerization, and terpolymerization, as well as processes that might also be referred to as oligomerization processes. Therefore, a copolymerization process can involve contacting an olefin monomer (e.g., ethylene) and an olefin comonomer (e.g., 1-hexene) to produce an olefin copolymer.

The term "co-catalyst" is used generally herein to refer to compounds such as aluminoxane compounds, organoboron or organoborate compounds, ionizing ionic compounds, organoaluminum compounds, organozinc compounds, organomagnesium compounds, organolithium compounds, and the like, that can constitute one component of a catalyst composition, when used, for example, in addition to an activator-support. The term "co-catalyst" is used regardless of the actual function of the compound or any chemical mechanism by which the compound may operate.

The term "activator-support" is used herein to indicate a solid, inorganic oxide of relatively high porosity, which can exhibit Lewis acidic or Brønsted acidic behavior, and which has been treated with an electron-withdrawing component, typically an anion, and which is calcined. The electron-withdrawing component is typically an electron-withdrawing anion source compound. Thus, the activator-support can comprise a calcined contact product of at least one solid oxide with at least one electron-withdrawing anion source compound. The terms "support" and "activator-support" are not used to imply these components are inert, and such components should not be construed as an inert component of the catalyst composition. The term "activator," as used herein, refers generally to a substance that is capable of converting a metallocene component into a catalyst that can polymerize olefins, or converting a contact product of a metallocene component and a component that provides an activatable ligand (e.g., an alkyl, a hydride) to the metallocene, when the metallocene compound does not already comprise such a ligand, into a catalyst that can polymerize olefins. This term is used regardless of the actual activating mechanism. Illustrative activators include activator-supports, aluminoxanes, organoboron or organoborate compounds, ionizing ionic compounds, and the like. Aluminoxanes, organoboron or organoborate compounds, and ionizing ionic compounds generally are referred to as activators if used in a catalyst composition in which an activator-support is not present. If the catalyst composition contains an activator-support, then the aluminoxane, organoboron or organoborate, and ionizing ionic materials are typically referred to as co-catalysts.

The term "metallocene" as used herein describes compounds comprising at least one $\eta^3$ to $\eta^5$-cycloalkadienyl-type moiety, wherein $\eta^3$ to $\eta^5$-cycloalkadienyl moieties include cyclopentadienyl ligands, indenyl ligands, fluorenyl ligands, and the like, including partially saturated or substituted derivatives or analogs of any of these. Possible substituents on these ligands can include H, therefore this invention comprises ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like. All cyclopentadienyl, indenyl, and fluorenyl groups are meant to encompass substituted or unsubstituted cyclopentadienyl, indenyl, and fluorenyl groups, unless stated otherwise. In some contexts, the metallocene can be referred to simply as the "catalyst," in much the same way the term "co-catalyst" can be used herein to refer to, for example, an organoaluminum compound.

In this disclosure, an "exposed" solid metallocene compound refers to a solid metallocene compound that has been exposed to air (oxygen, moisture), and the exposed solid metallocene compound may be partially hydrolyzed and/or may exhibit a color change (although not required), as compared to a "fresh" solid metallocene compound. The "fresh" solid metallocene compound is the reference or standard metallocene compound, unexposed to air, and generally stored under an inert gas such as nitrogen. A "treated" solid metallocene compound refers to the "exposed" solid metallocene compound after it has been treated in accordance with the methods disclosed herein, and also can be referred to as being recovered or restored.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the co-catalyst, the metallocene compound, or the activator (e.g., activator-support), after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, can be used interchangeably throughout this disclosure.

The terms "contact product," "contacting," and the like, are used herein to describe methods and compositions wherein the components are combined or contacted together in any order, in any manner, and for any length of time, unless otherwise specified. For example, the components can be contacted by blending or mixing. Further, unless otherwise specified, the contacting of any component can occur in the presence or absence of any other component of the methods and compositions described herein. Combining additional materials or components can be done by any suitable method. These terms encompass materials which can be blended, mixed, slurried, dissolved, reacted, treated, or otherwise contacted in some other manner.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

Several types of ranges are disclosed herein. When a range of any type is disclosed or claimed herein, the intent is to disclose or claim individually each possible number that such a range could reasonably encompass, including end points of the range as well as any sub-ranges and combinations of sub-ranges encompassed therein, unless otherwise specified. As a representative example, the present disclosure sets forth that the purging step can be performed at a purging temperature in a range from about 10° C. to about 75° C., in certain aspects. By a disclosure that the purging temperature can be in a range from about 10° C. to about 75° C., the intent is to recite that the purging temperature can be any temperature within the range and, for example, can be equal to about 10° C., about 20° C., about 30° C., about 40° C., about 50° C., about 60° C., about 70° C., or about 75° C. Additionally, the purging temperature can be within any range from about 10° C. to about 75° C. (for example, the temperature can be in a range from about 15° C. to about 50° C.), and this also includes any combination of ranges between about 10° C. to about 75° C. Likewise, all other ranges disclosed herein should be interpreted in a manner similar to this example.

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, and often within 5% of the reported numerical value.

DETAILED DESCRIPTION OF THE INVENTION

Disclosed herein are methods for treating solid metallocene compounds that have been exposed to air (e.g., oxygen and moisture), without utilizing a recrystallization process. Beneficially, catalyst solutions prepared from the treated solid metallocene compounds of this invention typically have comparable color, moisture level, long-term stability, and/or catalyst activity to that of solutions prepared from fresh and unexposed samples of the respective metallocene compounds that have been stored under nitrogen. Other potential benefits of the methods disclosed herein are readily apparent to those of skill in the art in view of this disclosure.
Methods for Treating Exposed Solid Metallocene Compounds Various methods for treating an exposed solid metallocene compound are disclosed and described herein. A first method for treating an exposed solid metallocene compound can comprise (or consist essentially of, or consist of) contacting the exposed solid metallocene compound with a purging gas stream comprising (or consisting essentially of, or consisting of) an inert gas to form a treated solid metallocene compound.

Generally, the features of the first method (e.g., the exposed solid metallocene compound, the treated solid metallocene compound, the conditions under which the exposed solid metallocene compound is contacted with the purging gas stream, and the inert gas, among others) are independently described herein, and these features may be combined in any combination to further describe this first method. Moreover, other process steps may be conducted before, during, and/or after the step listed in the first method, unless stated otherwise. Additionally, treated solid metallocene compounds prepared in accordance with this first method are within the scope of this disclosure and are encompassed herein.

The step in the first method in which the exposed solid metallocene compound is contacted with a purging gas stream often is referred to herein as a purging step. Additionally, any compositional attributes of the purging gas stream are meant to refer to the incoming purging gas steam, prior to contacting the exposed solid metallocene compound, unless expressly stated otherwise. As one of skill in the art would readily recognize, the outgoing purging gas stream, after contacting exposed solid metallocene compound, can vary significantly in composition from the incoming purging gas stream.

The purging step generally can comprise contacting the exposed solid metallocene compound with a purging gas stream comprising (or consisting essentially of, or consisting of) an inert gas. The inert gas can be helium, neon, argon, or nitrogen, or a mixture thereof; alternatively, helium; alternatively, neon; alternatively, argon; or alternatively, nitrogen.

Additionally, in some aspects, the purging gas stream can be substantially free of oxygen-containing compounds (e.g., $O_2$), i.e., the purging gas stream can contain less than 50 ppmw (ppm by weight) of oxygen-containing compounds. Therefore, it is contemplated that the amount of oxygen-containing compounds in the purging gas stream can be less than or equal to 25 ppmw, less than or equal to 10 ppmw, less than or equal to 5 ppmw, less than or equal to 3 ppmw, or less than or equal to 1 ppmw, in certain aspects. While not wishing to be bound by the following theory, it can be beneficial to have substantially no oxygen added during the purging step to treat the exposed solid metallocene compound. In particular aspects of this invention, therefore, it can be beneficial for the purging gas stream to contain less than or equal to 15 ppmw of oxygen-containing compounds; alternatively, less than or equal to 10 ppmw of oxygen-containing compounds; alternatively, less than or equal to 5 ppmw of oxygen-containing compounds; or alternatively, less than or equal to 1 ppmw of oxygen-containing compounds.

Moreover, although not required, the purging gas stream can be substantially free of water (moisture), i.e., the purging gas stream can contain less than 50 ppmw (ppm by weight) of water. As above, it is contemplated that the amount of water in the purging gas stream can be less than or equal to 25 ppmw, less than or equal to 10 ppmw, less than or equal to 5 ppmw, less than or equal to 3 ppmw, or less than or equal to 1 ppmw, in certain aspects. While not wishing to be bound by the following theory, it can be beneficial to have substantially water or moisture added during the purging step to treat the exposed solid metallocene compound. In particular aspects of this invention, therefore, it can be beneficial for the purging gas stream to contain less than or equal to 15 ppmw of water; alternatively, less than or equal to 10 ppmw of water; alternatively, less than or equal to 5 ppmw of water; or alternatively, less than or equal to 1 ppmw of water.

The purging step can be conducted at a variety of temperatures and time periods. For instance, the purging step can be conducted at a purging temperature in a range from about 0° C. to about 100° C.; alternatively, from about 0° C. to about 75° C.; alternatively, from about 10° C. to about 75° C.; alternatively, from about 20° C. to about 60° C.; alternatively, from about 20° C. to about 50° C.; alternatively, from about 15° C. to about 50° C.; or alternatively, from about 20° C. to about 40° C. In these and other aspects, these temperature ranges also are meant to encompass circumstances where the purging step is conducted at a series of different temperatures, instead of at a single fixed temperature, falling within the respective ranges. Further, while not wishing to be bound by the following theory, it is believed that the stability of the metallocene compound can be impacted by exposure to elevated temperatures, and therefore, excessive temperatures should be avoided, or if experienced, only for short durations.

The duration of the purging step is not limited to any particular period of time. Typically, the purging step can be conducted in a time period ranging from as little as 15-30 minutes to as long as 48-72 hours (or more), but more typically, the purging step can be conducted in a time period ranging from about 15 min to about 72 hours, such as, for example, from about 30 min to about 48 hours, from about 1 hour to about 24 hours, from about 1 hour to about 12 hours, from about 2 hours to about 8 hours, from about 30 min to about 3 hours, from about 15 min to about 6 hours, or from about 1 hour to about 6 hours.

Alternatively, the purging step can be conducted for a time period sufficient to reach at least 80% of the catalyst activity of a fresh solid metallocene compound, after 24 hours in a toluene solution, under the same polymerization conditions. That is, the purging step can be performed on the exposed solid metallocene compound for a time period sufficient for the catalyst activity of the treated solid metallocene compound to be at least 80% of the catalyst activity of a fresh solid metallocene compound. The catalyst activities for the treated solid metallocene compound and the fresh solid metallocene compound are tested on a solution containing 1 mg of metallocene in 1 mL of toluene, after storage under nitrogen for 24 hours at 25° C. The same polymerization conditions refer to slurry polymerization conditions, using isobutane as a diluent, and with a polymerization temperature of 90° C. and a reactor pressure of 390 psig. Moreover, all components used to prepare the catalyst systems are held constant (e.g., same amount of metallocene compound, same amount/type of organoaluminum (e.g., TIBA), same amount/type of activator-support (e.g., fluorided silica-coated alumina) and all polymerization conditions are held constant (e.g., same polymerization temperature, same pressure). Hence, the only difference is the use of the fresh solid metallocene compound instead of the treated solid metallocene compound.

In further aspects, the purging step can be conducted for a time period sufficient to reach at least 85%, at least 90%, or at least 95%, of the catalyst activity of the fresh solid metallocene compound, after 24 hours in a toluene solution, under the same polymerization conditions.

In another aspect, the purging step can be conducted for a time period sufficient to maintain the color of a 1 mg/mL solution of the treated solid metallocene compound for at least 24 hours at 25° C. That is, the purging step can be performed on the exposed solid metallocene compound for a time period sufficient for the treated solid metallocene compound to maintain its color (i.e., visually, the same color as that of the fresh solid metallocene compound) in a 1 mg/mL solution of the treated solid metallocene compound for at least 24 hours at 25° C. (stored under nitrogen). The solvent can be any suitable solvent for the metallocene compound, but often, toluene can be used.

In further aspects, the purging step can be conducted for a time period sufficient to maintain the color of a 1 mg/mL solution of the treated solid metallocene compound for 24 hours, for 30 hours, for 36 hours, or for 48 hours, at 25° C.

The purging step can be performed in any suitable vessel or container, and any method known to a skilled artisan for contacting the exposed solid metallocene compound with the purging gas stream can be utilized. In one aspect, for instance, the exposed solid metallocene compound can be placed in a vessel and the purging gas can be introduced into the vessel to contact the solid material. In another aspect, the exposed solid metallocene compound can be placed in a vessel in a fixed bed arrangement, and the purging gas can be flowed through the fixed bed of the solid material. In yet another aspect, the exposed solid metallocene compound can be placed in a vessel, and the solid material can be fluidized with the purging gas stream.

A second method for treating an exposed solid metallocene compound can comprise (or consist essentially of, or consist of), in any order:

contacting the exposed solid metallocene compound with a purging gas stream comprising (or consisting essentially of, or consisting of) an inert gas; and subjecting the exposed solid metallocene compound to a sub-atmospheric pressure; to form a treated solid metallocene compound.

Generally, the features of the second method (e.g., the exposed solid metallocene compound, the treated solid metallocene compound, the conditions under which the exposed solid metallocene compound is contacted with the purging gas stream, the inert gas, and the conditions under which the exposed solid metallocene compound is exposed to sub-atmospheric pressure, among others) are independently described herein, and these features may be combined in any combination to further describe this second method. Moreover, other process steps may be conducted before, during, and/or after the steps listed in the second method, unless stated otherwise. Additionally, treated solid metallocene compounds prepared in accordance with this second method are within the scope of this disclosure and are encompassed herein.

Any characteristics or features of the purging step in this second method for treating an exposed solid metallocene compound can be the same as those described herein for the purging step in the first method for treating an exposed solid metallocene compound. Additionally, the step in the second method in which the exposed solid metallocene compound is subjected to a sub-atmospheric pressure often is referred to herein as a vacuum step.

The subjecting step (or vacuum step) in the second method for treating an exposed solid metallocene compound can comprise subjecting the exposed solid metallocene compound to any suitable sub-atmospheric pressure. For instance, and not limited thereto, the pressure can be less than 100 torr, less than 50 torr, less than 10 torr, or less than 1 torr. Illustrative pressure ranges can include, for example, from about 100 to about 0.01 torr, from about 10 to about 0.1 torr, or from about 1 to about 0.1 torr.

The subjecting step (or vacuum step) can be conducted at a variety of temperatures and time periods. For instance, the subjecting step can be conducted at a vacuum temperature in a range from about 0° C. to about 100° C.; alternatively, from about 0° C. to about 75° C.; alternatively, from about 10° C. to about 75° C.; alternatively, from about 20° C. to about 60° C.; alternatively, from about 20° C. to about 50° C.; alternatively, from about 15° C. to about 50° C.; or alternatively, from about 20° C. to about 40° C. In these and other aspects, these temperature ranges also are meant to encompass circumstances where the vacuum step is conducted at a series of different temperatures, instead of at a single fixed temperature, falling within the respective ranges. Further, while not wishing to be bound by the following theory, it is believed that the stability of the metallocene compound can be impacted by exposure to elevated temperatures, and therefore, excessive temperatures should be avoided, or if experienced, only for short durations.

The duration of the subjecting step (or vacuum step) is not limited to any particular period of time, and the duration can vary depending upon the vacuum temperature and the sub-atmospheric pressure used (e.g., 0.5 torr versus 50 torr). Typically, the subjecting step can be conducted in a time period ranging from as little as 15-30 minutes to as long as 48-72 hours (or more), but more typically, the subjecting step can be conducted in a time period ranging from about 15 min to about 72 hours, such as, for example, from about 30 min to about 48 hours, from about 1 hour to about 24 hours, from about 1 hour to about 12 hours, from about 2 hours to about 8 hours, from about 30 min to about 3 hours, from about 15 min to about 6 hours, or from about 1 hour to about 6 hours.

The second method can be conducted by performing any number of contacting (purging) cycles and any number of subjecting (vacuum) cycles, and these cycles can be performed in any order or sequence. Thus, the method can comprise from 1 to 8, from 1 to 6, from 1 to 4, from 2 to 6, or from 2 to 4, contacting (purging) cycles and from 1 to 8, from 1 to 6, from 1 to 4, from 2 to 6, or from 2 to 4, subjecting (vacuum) cycles. Each contacting (purging) cycle and each subjecting (vacuum) cycle, independently, can be performed at any condition disclosed herein (e.g., temperature, time, etc.) for the respective contacting (purging) step and subjecting (vacuum) step.

As an example, the second method for treating an exposed solid metallocene compound can comprise a first contacting (purging) cycle, a first subjecting (vacuum) cycle, a second contacting (purging) cycle, a second subjecting (vacuum) cycle, and a third contacting (purging) cycle. Each of these cycles can be performed at any temperature, pressure, and time duration disclosed herein.

As another example, the second method for treating an exposed solid metallocene compound can comprise a first subjecting (vacuum) cycle, a first contacting (purging) cycle, a second subjecting (vacuum) cycle, and a second contacting (purging) cycle. Each of these cycles can be performed at any temperature, pressure, and time duration disclosed herein.

The first method for treating an exposed solid metallocene compound and the second method for treating an exposed solid metallocene compound, independently, can be conducted under conditions sufficient (e.g., temperature, pressure, time, cycles, etc.) to reach at least 80% of the catalyst activity of a fresh solid metallocene compound, after 24 hours in a toluene solution, under the same polymerization conditions. That is, the first method for treating an exposed solid metallocene compound and the second method for treating an exposed solid metallocene compound, independently, can be conducted such that the catalyst activity of the treated solid metallocene compound can be at least 80% of the catalyst activity of a fresh solid metallocene compound. The catalyst activities for the treated solid metallocene compound and the fresh solid metallocene compound are tested on a solution containing 1 mg of metallocene in 1 mL of toluene, after storage under nitrogen for 24 hours at 25° C. The same polymerization conditions refer to slurry polymerization conditions, using isobutane as a diluent, and with a polymerization temperature of 90° C. and a reactor pressure of 390 psig. Moreover, all components used to prepare the catalyst systems are held constant (e.g., same amount of metallocene compound, same amount/type of organoaluminum (e.g., TIBA), same amount/type of activator-support (e.g., fluorided silica-coated alumina) and all polymerization conditions are held constant (e.g., same polymerization temperature, same pressure). Hence, the only difference is the use of the fresh solid metallocene compound instead of the treated solid metallocene compound.

In further aspects, the first method for treating an exposed solid metallocene compound and the second method for treating an exposed solid metallocene compound, independently, can be conducted under conditions sufficient to reach at least 85%, at least 90%, or at least 95%, of the catalyst activity of the fresh solid metallocene compound, after 24 hours in a toluene solution, under the same polymerization conditions.

In another aspect, the first method for treating an exposed solid metallocene compound and the second method for treating an exposed solid metallocene compound, independently, can be conducted under conditions sufficient to maintain the color of a 1 mg/mL solution of the treated solid metallocene compound for at least 24 hours at 25° C. That is, the first method and the second method, independently, can be performed on the exposed solid metallocene compound under conditions sufficient for the treated solid metallocene compound to maintain its color (i.e., visually, the same color as that of the fresh solid metallocene compound) in a 1 mg/mL solution of the treated solid metallocene compound for at least 24 hours at 25° C. (stored under nitrogen). The solvent can be any suitable solvent for the metallocene compound, but often, toluene can be used.

In further aspects, the first method for treating an exposed solid metallocene compound and the second method for treating an exposed solid metallocene compound, independently, can be conducted under conditions sufficient to maintain the color of a 1 mg/mL solution of the treated solid metallocene compound for 24 hours, for 30 hours, for 36 hours, or for 48 hours, at 25° C.

Consistent with aspects of this invention, both the first method for treating an exposed solid metallocene compound and the second method for treating an exposed solid metallocene compound do not require or use a recrystallization step.

The treated solid metallocene compound prepared by the first method and the second method can be characterized by very low moisture levels, and such can be quantified by the moisture level of a solution containing the treated solid metallocene compound. A 1 mg/mL solution of the treated solid metallocene compound is prepared at 25° C. under nitrogen. The solvent can be any suitable solvent for the metallocene compound, but often, toluene can be used. The first and second methods disclosed herein can result in a substantially moisture-free treated solid metallocene compound, characterized by a 1 mg/mL solution of the treated solid metallocene compound having a moisture level of less than 15 ppmw (ppm by weight). In some aspects, the moisture level of a 1 mg/mL solution of the treated solid metallocene can be less than or equal to 10 ppmw, less than or equal to 8 ppmw, less than or equal to 4 ppmw, less than or equal to 2 ppmw, or no measurable amount of moisture. While not wishing to be bound by the following theory, it is believed that longer-term stability of the metallocene solution can be improved when the moisture level of the solution in less than or equal to 5 ppmw, and even more so, when the moisture level of the solution is less than or equal to 2 ppmw.

Catalyst Compositions

Catalyst compositions containing the treated solid metallocene compound and processes for producing catalyst compositions using the treated solid metallocene compound also are encompassed herein. For instance, one such process to produce a catalyst composition can comprise contacting, in any order, (a) any treated solid metallocene compound disclosed herein, (b) any activator disclosed herein, and (c) optionally, any co-catalyst disclosed herein, to produce the catalyst composition.

In the preparation of the catalyst composition, the treated solid metallocene compound can be present as a slurry in a diluent in one aspect of this invention, while in another aspect of this invention, the treated solid metallocene compound can be present as a metallocene solution in a suitable solvent.

Generally, catalyst compositions of the present invention comprise a treated solid metallocene compound and an activator. In aspects of the invention, the activator can comprise an activator-support (e.g., an activator-support comprising a solid oxide treated with an electron-withdrawing anion). Activator-supports useful in the present invention are disclosed herein. Optionally, such catalyst compositions can further comprise one or more than one co-catalyst compound or compounds (suitable co-catalysts, such as organoaluminum compounds, also are discussed herein). Thus, a catalyst composition of this invention can comprise a treated solid metallocene compound, an activator-support, and an organoaluminum compound. For instance, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided-chlorided silica-coated alumina, fluorided silica-coated alumina, sulfated silica-coated alumina, phosphated silica-coated alumina, and the like, or combinations thereof; or alternatively, a fluorided solid oxide and/or a sulfated solid oxide. Additionally, the organoaluminum compound can comprise (or consist essentially of, or consist of) trimethylaluminum, triethylaluminum, tri-n-propylaluminum, tri-n-butyl aluminum, triisobutylaluminum, tri-n-hexylaluminum, tri-n-octylaluminum, diisobutylaluminum hydride, diethylaluminum ethoxide, diethylaluminum chloride, and the like, or combinations thereof. Accordingly, a catalyst composition consistent with aspects of the invention can comprise (or consist essentially of, or consist of) a treated solid metallocene compound; sulfated alumina (or fluorided-chlorided silica-coated alumina, or fluorided silica-coated alumina); and triethylaluminum (or triisobutylaluminum).

In another aspect of the present invention, a catalyst composition is provided which comprises a treated solid metallocene compound, an activator-support, and an organoaluminum compound, wherein this catalyst composition is substantially free of aluminoxanes, organoboron or organoborate compounds, ionizing ionic compounds, and/or other similar materials; alternatively, substantially free of aluminoxanes; alternatively, substantially free or organoboron or organoborate compounds; or alternatively, substantially free of ionizing ionic compounds. In these aspects, the catalyst composition has catalyst activity, discussed herein, in the absence of these additional materials. For example, a catalyst composition of the present invention can consist essentially of a treated solid metallocene compound, an activator-support, and an organoaluminum compound, wherein no other materials are present in the catalyst composition which would increase/decrease the activity of the catalyst composition by more than about 10% from the catalyst activity of the catalyst composition in the absence of said materials.

However, in other aspects of this invention, these activators/co-catalysts can be employed. For example, a catalyst composition comprising a treated solid metallocene compound and an activator-support can further comprise a co-catalyst. Suitable co-catalysts in this aspect can include, but are not limited to, aluminoxane compounds, organoboron or organoborate compounds, ionizing ionic compounds, organoaluminum compounds, organozinc compounds, organomagnesium compounds, organolithium compounds, and the like, or any combination thereof; or alternatively, organoaluminum compounds, organozinc compounds, organomagnesium compounds, organolithium compounds, or any combination thereof. More than one co-catalyst can be present in the catalyst composition.

In a different aspect, a catalyst composition is provided which does not require an activator-support. Such catalyst composition can comprise a treated solid metallocene compound and an activator, wherein the activator can comprise an aluminoxane compound (e.g., a supported aluminoxane), an organoboron or organoborate compound, an ionizing ionic compound, or combinations thereof; alternatively, an aluminoxane compound; alternatively, an organoboron or organoborate compound; or alternatively, an ionizing ionic compound.

Metallocene Compounds

As discussed herein, the metallocene compound can be described as an exposed metallocene compound, a treated metallocene compound, or a fresh metallocene compound. Regardless of the nomenclature or terminology, it is believed that any solid metallocene compound that has been exposed to air and/or moisture can benefit from the methods disclosed herein, regardless of its chemical structure.

Accordingly, the metallocene compound can comprise a bridged metallocene compound and/or an unbridged metallocene compound. The metallocene compound can comprise, for example, a transition metal (one or more than one) from Groups 3-8 of the Periodic Table of the Elements. In one aspect, the metallocene compound can comprise a Group 3 to Group 6 transition metal, or a combination of two or more transition metals. The metallocene compound can comprise chromium, titanium, zirconium, hafnium, vanadium, or a combination thereof, or can comprise titanium, zirconium, hafnium, or a combination thereof, in other aspects. In further aspects, the metallocene compound can comprise titanium, or zirconium, or hafnium, either singly or in combination.

In some aspects of this invention, the metallocene compound can comprise a bridged metallocene compound, e.g., with titanium, zirconium, or hafnium, such as a bridged zirconium or hafnium based metallocene compound with a fluorenyl group, and with no aryl groups on the bridging group, or a bridged zirconium or hafnium based metallocene compound with a cyclopentadienyl group and a fluorenyl group, and with no aryl groups on the bridging group. Such bridged metallocenes, in some aspects, can contain an alkenyl substituent (e.g., a terminal alkenyl) on the bridging group and/or on a cyclopentadienyl-type group (e.g., a cyclopentadienyl group or a fluorenyl group). In another aspect, the metallocene compound can comprise a bridged zirconium or hafnium based metallocene compound with a fluorenyl group, and an aryl group on the bridging group; alternatively, a bridged zirconium or hafnium based metallocene compound with a cyclopentadienyl group and fluorenyl group, and an aryl group on the bridging group; alternatively, a bridged zirconium based metallocene compound with a fluorenyl group, and an aryl group on the bridging group; or alternatively, a bridged hafnium based metallocene compound with a fluorenyl group, and an aryl group on the bridging group. In these and other aspects, the aryl group on the bridging group can be a phenyl group. Optionally, these bridged metallocenes can contain an alkenyl substituent (e.g., a terminal alkenyl) on the bridging group and/or on a cyclopentadienyl-type group.

In some aspects, the metallocene compound can comprise a bridged zirconium or hafnium based metallocene compound with two indenyl groups (e.g., a bis-indenyl metallocene compound). Hence, the metallocene compound can comprise a bridged zirconium based metallocene compound with two indenyl groups, or alternatively, a bridged hafnium based metallocene compound with two indenyl groups. In some aspects, an aryl group can be present on the bridging group, while in other aspects, there are no aryl groups present on the bridging group. Optionally, these bridged indenyl metallocenes can contain an alkenyl substituent (e.g., a terminal alkenyl) on the bridging group and/or on the indenyl group (one or both indenyl groups). The bridging atom of the bridging group can be, for instance, a carbon atom or a silicon atom; alternatively, the bridge can contain a chain of two carbon atoms, a chain of two silicon atoms, and so forth.

Illustrative and non-limiting examples of bridged metallocene compounds (e.g., with zirconium or hafnium) that can be used in methods consistent with aspects of the present invention are described in U.S. Pat. Nos. 7,026,494, 7,041,617, 7,226,886, 7,312,283, 7,517,939, and 7,619,047, the disclosures of which are incorporated herein by reference in their entirety.

In some aspects of this invention, the metallocene compound can comprise an unbridged metallocene; alternatively, an unbridged zirconium or hafnium based metallocene compound and/or an unbridged zirconium and/or hafnium based dinuclear metallocene compound; alternatively, an unbridged zirconium or hafnium based metallocene compound containing two cyclopentadienyl groups, two indenyl groups, or a cyclopentadienyl and an indenyl group; alternatively, an unbridged zirconium based metallocene compound containing two cyclopentadienyl groups, two indenyl groups, or a cyclopentadienyl and an indenyl group. Illustrative and non-limiting examples of unbridged metallocene compounds (e.g., with zirconium or hafnium) that can be used in methods consistent with aspects of the present invention are described in U.S. Pat. Nos. 7,199,073, 7,226,886, 7,312,283, and 7,619,047, the disclosures of which are incorporated herein by reference in their entirety.

Moreover, the metallocene compound can comprise an unbridged dinuclear metallocene such as those described in U.S. Pat. Nos. 7,919,639 and 8,080,681, the disclosures of which are incorporated herein by reference in their entirety. The metallocene compound can comprise an unbridged zirconium and/or hafnium based dinuclear metallocene compound. For example, the metallocene compound can comprise an unbridged zirconium based homodinuclear metallocene compound, or an unbridged hafnium based homodinuclear metallocene compound, or an unbridged zirconium and/or hafnium based heterodinuclear metallocene compound (i.e., a dinuclear compound with two hafniums, or two zirconiums, or one zirconium and one hafnium).

Activator-Supports

The present invention encompasses various catalyst compositions containing an activator-support. In one aspect, the activator-support can comprise a solid oxide treated with an electron-withdrawing anion. Alternatively, in another aspect, the activator-support can comprise a solid oxide treated with an electron-withdrawing anion, the solid oxide containing a Lewis-acidic metal ion. Non-limiting examples of suitable activator-supports are disclosed in, for instance, U.S. Pat. Nos. 7,294,599, 7,601,665, 7,884,163, 8,309,485, 8,623,973, 8,703,886, and 9,023,959, which are incorporated herein by reference in their entirety.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form an activator-support, either singly or in combination, can include, but are not limited to, silica-alumina, silica-titania, silica-zirconia, alumina-titania, alumina-zirconia, zinc-aluminate, alumina-boria, silica-boria, aluminophosphate-silica, titania-zirconia, and the like. The solid oxide used herein also encompasses oxide materials such as silica-coated alumina, as described in U.S. Pat. No. 7,884,163 (e.g., Sasol Siral® 28, Sasol Siral® 40, etc.).

Accordingly, in one aspect, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another aspect, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. In another aspect, the solid oxide can comprise silica, alumina, titania, zirconia, magnesia, boria, zinc oxide, any mixed oxide thereof, or any combination thereof. In yet another aspect, the solid oxide can comprise silica-alumina, silica-coated alumina, silica-titania, silica-zirconia, alumina-boria, or any combination thereof. In still another aspect, the solid oxide can comprise alumina, silica-alumina, silica-coated alumina, or any mixture thereof; alternatively, alumina; alternatively, silica-alumina; or alternatively, silica-coated alumina.

The silica-alumina or silica-coated alumina solid oxide materials which can be used can have an silica content from about 5 to about 95% by weight. In one aspect, the silica content of these solid oxides can be from about 10 to about 80%, or from about 20% to about 70%, silica by weight. In another aspect, such materials can have silica contents ranging from about 15% to about 60%, from about 20% to about 50%, or from about 25% to about 45%, silica by weight. The solid oxides contemplated herein can have any suitable surface area, pore volume, and particle size, as would be recognized by those of skill in the art.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, molybdate, and the like, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The activator-support generally can contain from about 1 to about 25 wt. % of the electron-withdrawing anion, based on the weight of the activator-support. In particular aspects provided herein, the activator-support can contain from about 1 to about 20 wt. %, from about 2 to about 20 wt. %, from about 3 to about 20 wt. %, from about 2 to about 15 wt. %, from about 3 to about 15 wt. %, from about 3 to about 12 wt. %, or from about 4 to about 10 wt. %, of the electron-withdrawing anion, based on the total weight of the activator-support.

In an aspect, the activator-support can comprise fluorided alumina, chlorided alumina, bromided alumina, sulfated alumina, phosphated alumina, fluorided silica-alumina, chlorided silica-alumina, bromided silica-alumina, sulfated silica-alumina, phosphated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, and the like, as well as any mixture or combination thereof. In another aspect, the activator-support employed in the processes and catalyst systems described herein can be, or can comprise, a fluorided solid oxide and/or a sulfated solid oxide and/or a phosphated solid oxide, non-limiting examples of which can include fluorided alumina, sulfated alumina, phosphated alumina, fluorided silica-alumina, sulfated silica-alumina, phosphated silica-alumina, fluorided silica-zirconia, fluorided silica-coated alumina, fluorided-chlorided silica-coated alumina, sulfated silica-coated alumina, phosphated silica-coated alumina, and the like, as well as combinations thereof. In yet another aspect, the activator-support can comprise fluorided alumina; alternatively, chlorided alumina; alternatively, sulfated alumina; alternatively, phosphated alumina; alternatively, fluorided silica-alumina; alternatively, sulfated silica-alumina; alternatively, phosphated silica-alumina; alternatively, fluorided silica-zirconia; alternatively, chlorided silica-zirconia; alternatively, sulfated silica-coated alumina; alternatively, phosphated silica-coated alumina; alternatively, fluorided-chlorided silica-coated alumina; or alternatively, fluorided silica-coated alumina.

Various processes can be used to form activator-supports useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, and the like, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing activator-supports (e.g., fluorided solid oxides, sulfated solid oxides, etc.) are well known to those of skill in the art.

Co-Catalysts

In certain aspects directed to catalyst compositions containing a co-catalyst, the co-catalyst can comprise a metal hydrocarbyl compound, examples of which include non-halide metal hydrocarbyl compounds, metal hydrocarbyl halide compounds, non-halide metal alkyl compounds, metal alkyl halide compounds, and so forth. The hydrocarbyl group (or alkyl group) can be any hydrocarbyl (or alkyl) group disclosed herein. Moreover, in some aspects, the metal of the metal hydrocarbyl can be a group 1, 2, 11, 12, 13, or 14 metal; alternatively, a group 13 or 14 metal; or alternatively, a group 13 metal. Hence, in some aspects, the metal of the metal hydrocarbyl (or non-halide metal hydrocarbyl or metal hydrocarbyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some aspects, the metal hydrocarbyl or metal alkyl, with or without a halide, can comprise a lithium hydrocarbyl or alkyl, a magnesium hydrocarbyl or alkyl, a boron hydrocarbyl or alkyl, a zinc hydrocarbyl or alkyl, or an aluminum hydrocarbyl or alkyl.

In particular aspects directed to catalyst compositions containing a co-catalyst (e.g., the activator can comprise a solid oxide treated with an electron-withdrawing anion), the co-catalyst can comprise an aluminoxane compound (e.g., a supported aluminoxane), an organoboron or organoborate compound, an ionizing ionic compound, an organoaluminum compound, an organozinc compound, an organomagnesium compound, or an organolithium compound, and this includes any combinations of these materials. In one aspect, the co-catalyst can comprise an organoaluminum compound. In another aspect, the co-catalyst can comprise an aluminoxane compound, an organoboron or organoborate compound, an ionizing ionic compound, an organozinc compound, an organomagnesium compound, an organolithium compound, or any combination thereof. In yet another aspect, the co-catalyst can comprise an aluminoxane compound; alternatively, an organoboron or organoborate compound; alternatively, an ionizing ionic compound; alternatively, an organozinc compound; alternatively, an organomagnesium compound; or alternatively, an organolithium compound.

Specific non-limiting examples of suitable organoaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutyl aluminum hydride, di ethyl aluminum ethoxide, diethylaluminum chloride, and the like, or combinations thereof. Representative and non-limiting examples of aluminoxanes include methylaluminoxane, modified methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentyl aluminoxane, 2-pentylaluminoxane, 3-pentyl aluminoxane, isopentyl aluminoxane, neopentylaluminoxane, and the like, or any combination thereof. Representative and non-limiting examples of organoboron/organoborate compounds include N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, tris(pentafluorophenyl)boron, tris[3,5-bis(trifluoromethyl)phenyl]boron, and the like, or mixtures thereof.

Examples of ionizing ionic compounds can include, but are not limited to, the following compounds: tri(n-butyl)ammonium tetrakis(p-tolyl)borate, tri(n-butyl) ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoromethyl)phenyl]borate, triphenylcarbenium tetrakis(pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis(pentafluorophenyl) borate, lithium tetrakis(pentafluorophenyl)borate, lithium tetraphenylborate, lithium tetrakis(p-tolyl)borate, lithium tetrakis(m-tolyl)borate, lithium tetrakis(2,4-dim ethyl phenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis(pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis(pentafluorophenyl)aluminate, sodium tetraphenylaluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis(3,5-dimethylphenyl)aluminate, potassium tetrafluoroaluminate, and the like, or combinations thereof.

Exemplary organozinc compounds which can be used as co-catalysts can include, but are not limited to, dimethylzinc, diethylzinc, dipropylzinc, dibutylzinc, dineopentylzinc, di(trimethylsilyl)zinc, di(triethylsilyl)zinc, di(triisoproplysilyl)zinc, di(triphenylsilyl)zinc, di(allyldimethylsilyl)zinc, di(trimethylsilylmethyl)zinc, and the like, or combinations thereof.

Similarly, exemplary organomagnesium compounds can include, but are not limited to, dimethylmagnesium, diethylmagnesium, dipropylmagnesium, dibutylmagnesium, dineopentylmagnesium, di(trimethylsilylmethyl)magnesium, methylmagnesium chloride, ethylmagnesium chloride, propylmagnesium chloride, butylmagnesium chloride, neopentylmagnesium chloride, trimethylsilylmethylmagnesium chloride, methylmagnesium bromide, ethylmagnesium bromide, propylmagnesium bromide, butylmagnesium bromide, neopentylmagnesium bromide, trimethylsilylmethylmagnesium bromide, methylmagnesium iodide, ethylmagnesium iodide, propylmagnesium iodide, butylmagnesium iodide, neopentylmagnesium iodide, trimethylsilylmethylmagnesium iodide, methylmagnesium ethoxide, ethylmagnesium ethoxide, propylmagnesium ethoxide, butylmagnesium ethoxide, neopentylmagnesium ethoxide, trimethyl silylmethylmagnesium ethoxide, methylmagnesium propoxide, ethylmagnesium propoxide, propylmagnesium propoxide, butylmagnesium propoxide, neopentylmagnesium propoxide, trimethylsilylmethylmagnesium propoxide, methylmagnesium phenoxide, ethylmagnesium phenoxide, propylmagnesium phenoxide, butylmagnesium phenoxide, neopentylmagnesium phenoxide, trimethylsilylmethylmagnesium phenoxide, and the like, or any combinations thereof.

Likewise, exemplary organolithium compounds can include, but are not limited to, methyllithium, ethyllithium, propyllithium, butyllithium (e.g., t-butyllithium), neopentyllithium, trim ethyl silylmethyllithium, phenyllithium, tolyllithium, xylyllithium, benzyllithium, (dimethylphenyl)methyllithium, allyllithium, and the like, or combinations thereof.

Co-catalysts that can be used in the catalyst compositions of this invention are not limited to the co-catalysts described above. Other suitable co-catalysts are well known to those of skill in the art including, for example, those disclosed in U.S. Pat. Nos. 3,242,099, 4,794,096, 4,808,561, 5,576,259, 5,807,938, 5,919,983, 7,294,599 7,601,665, 7,884,163, 8,114,946, and 8,309,485, which are incorporated herein by reference in their entirety.

Olefin Monomers and Olefin Polymers

Olefin monomers contemplated herein typically include olefin compounds having from 2 to 30 carbon atoms per molecule and having at least one olefinic double bond. Homopolymerization processes using a single olefin, such as ethylene, propylene, butene, hexene, octene, and the like, are encompassed, as well as copolymerization and terpolymerization, reactions using an olefin monomer with at least one different olefinic compound. For example, resultant ethylene copolymers, or terpolymers, generally can contain a major amount of ethylene (>50 mole percent) and a minor amount of comonomer (<50 mole percent), though this is not a requirement. Comonomers that can be copolymerized with ethylene often can have from 3 to 20 carbon atoms, or from 3 to 10 carbon atoms, in their molecular chain.

Acyclic, cyclic, polycyclic, terminal (a), internal, linear, branched, substituted, unsubstituted, functionalized, and non-functionalized olefins can be employed. For example, typical unsaturated compounds that can be polymerized to produce olefin polymers can include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described herein. Styrene also can be employed as a monomer or as a comonomer. In an aspect, the olefin monomer can comprise a $C_2$-$C_{20}$ olefin; alternatively, a $C_2$-$C_{20}$ α-olefin; alternatively, a $C_2$-$C_{12}$ olefin; alternatively, a $C_2$-$C_{10}$ α-olefin; alternatively, ethylene, propylene, 1-butene, 1-hexene, or 1-octene; alternatively, ethylene or propylene; alternatively, ethylene; or alternatively, propylene.

When a copolymer (or alternatively, a terpolymer) is desired, the olefin monomer can be, for example, ethylene or propylene, which is copolymerized with at least one comonomer (e.g., a $C_2$-$C_{20}$ α-olefin, a $C_3$-$C_{20}$ α-olefin). According to one aspect, the olefin monomer in the polymerization process can be ethylene. In this aspect, examples of suitable olefin comonomers can include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to another aspect, the comonomer can comprise an α-olefin (e.g., a $C_3$-$C_{10}$ α-olefin), while in yet another aspect, the comonomer can comprise 1-butene, 1-pentene, 1-hexene, 1-octene, 1-decene, styrene, or any combination thereof. For example, the comonomer can comprise 1-butene, 1-hexene, 1-octene, or a combination thereof alternatively, the comonomer can comprise 1-butene; alternatively, the comonomer can comprise 1-hexene; or alternatively, the comonomer can comprise 1-octene.

Generally, the amount of comonomer introduced into a polymerization reactor to produce the copolymer can be from about 0.01 to about 50 weight percent of the comonomer based on the total weight of the monomer and comonomer. According to another aspect, the amount of comonomer introduced into a polymerization reactor can be from about 0.01 to about 40 weight percent comonomer based on the total weight of the monomer and comonomer. In still another aspect, the amount of comonomer introduced into a polymerization reactor can be from about 0.1 to about 35 weight percent comonomer based on the total weight of the monomer and comonomer. Yet, in another aspect, the amount of comonomer introduced into a polymerization reactor can be from about 0.5 to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization reaction. Thus, branched and/or cyclic portion(s) of the olefin removed somewhat from the carbon-carbon double bond would not be expected to hinder the reaction in the way that the same olefin substituents situated more proximate to the carbon-carbon double bond might.

According to one aspect, at least one monomer/reactant can be ethylene (or propylene), so the polymerization reaction can be a homopolymerization involving only ethylene (or propylene), or a copolymerization with a different acyclic, cyclic, terminal, internal, linear, branched, substituted, or unsubstituted olefin. In addition, the methods disclosed herein intend for olefin to also encompass diolefin compounds that include, but are not limited to, 1,3-butadiene, isoprene, 1,4-pentadiene, 1,5-hexadiene, and the like.

Olefin polymers encompassed herein can include any polymer (or oligomer) produced from any olefin monomer (and optional comonomer(s)) described herein. For example, the olefin polymer can comprise an ethylene homopolymer, a propylene homopolymer, an ethylene copolymer (e.g., ethylene/α-olefin, ethylene/1-butene, ethylene/1-hexene, or ethylene/1-octene), a propylene copolymer, an ethylene terpolymer, a propylene terpolymer, and the like, including combinations thereof. In one aspect, the olefin polymer can be (or can comprise) an ethylene homopolymer, an ethylene/1-butene copolymer, an ethylene/1-hexene copolymer, or an ethyl ene/l-octene copolymer; or alternatively, an ethylene/1-hexene copolymer. In another aspect, the olefin polymer can be (or can comprise) a polypropylene homopolymer or a propylene-based copolymer. In some aspects, the olefin polymer can have a bimodal molecular weight distribution, while in other aspects, the olefin polymer can have a multimodal molecular weight distribution. Yet, in still other aspects, the olefin polymer can have a unimodal molecular weight distribution.

Polymerization Reactor Systems and Processes

The disclosed catalyst systems and methods of their preparation are intended for any olefin polymerization process using various types of polymerization reactors, polymerization reactor systems, and polymerization reaction conditions. As used herein, "polymerization reactor" includes any polymerization reactor capable of polymerizing olefin monomers and comonomers (one or more than one comonomer) to produce homopolymers, copolymers, terpolymers, and the like. The various types of polymerization reactors include, but are not limited to, those that can be referred to as a batch reactor, slurry reactor, gas-phase reactor, solution reactor, high pressure reactor, tubular reactor, autoclave reactor, and the like, or combinations thereof. Suitable polymerization conditions are used for the various reactor types. Gas phase reactors can comprise fluidized bed reactors or staged horizontal reactors. Slurry reactors can comprise vertical or horizontal loops. High pressure reactors can comprise autoclave reactors, tubular reactors, or combinations thereof, in parallel or in series. Reactor types can include batch or continuous processes. Continuous processes can use intermittent or continuous product discharge. Polymerization reactor systems and processes also can include partial or full direct recycle of unreacted monomer, unreacted comonomer, and/or diluent.

A polymerization reactor system can comprise a single reactor or multiple reactors (for example, 2 reactors, or more than 2 reactors) of the same or different type. For example, the polymerization reactor system can comprise a slurry reactor, a gas-phase reactor, a solution reactor, or a combination of two or more of these reactors. Production of polymers in multiple reactors can include several stages in at least two separate polymerization reactors interconnected by at least one transfer device, making it possible to transfer the polymers resulting from the first polymerization reactor into the second reactor. The desired polymerization conditions in one of the reactors can be different from the operating conditions of the other reactor(s). Alternatively, polymerization in multiple reactors can include the manual transfer of polymer from one reactor to subsequent reactors for continued polymerization. Multiple reactor systems can include any combination including, but not limited to, multiple loop reactors, multiple gas phase reactors, a combination of loop and gas phase reactors, multiple high pressure reactors, or a combination of high pressure with loop and/or gas phase reactors. The multiple reactors can be operated in series, in parallel, or both.

According to one aspect, the polymerization reactor system can comprise at least one loop slurry reactor comprising vertical or horizontal loops. Monomer, diluent, catalyst, and comonomer can be continuously fed into a loop reactor where polymerization occurs. Generally, continuous processes can comprise the continuous introduction of monomer/comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer and/or comonomer. Various technologies can be used for this separation step including, but not limited to, flashing that can include any combination of heat addition and pressure reduction, separation by cyclonic action in either a cyclone or hydrocyclone, or separation by centrifugation.

A typical slurry polymerization process (also known as the particle form process) is disclosed, for example, in U.S. Pat. Nos. 3,248,179, 4,501,885, 5,565,175, 5,575,979, 6,239,235, 6,262,191, 6,833,415, and 8,822,608, each of which is incorporated herein by reference in its entirety.

Suitable diluents used in slurry polymerization include, but are not limited to, the monomer being polymerized and hydrocarbons that are liquids under polymerization conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used, such as can be employed in the bulk polymerization of propylene to form polypropylene homopolymers.

According to yet another aspect, the polymerization reactor system can comprise at least one gas phase reactor (e.g., a fluidized bed reactor). Such reactor systems can employ a continuous recycle stream containing one or more monomers continuously cycled through a fluidized bed in the presence of the catalyst under polymerization conditions. A recycle stream can be withdrawn from the fluidized bed and recycled back into the reactor. Simultaneously, polymer product can be withdrawn from the reactor and new or fresh monomer can be added to replace the polymerized monomer. Such gas phase reactors can comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. Representative gas phase reactors are disclosed in U.S. Pat. Nos. 5,352,749, 4,588,790, 5,436,304, 7,531,606, and 7,598,327, each of which is incorporated by reference in its entirety herein.

According to still another aspect, the polymerization reactor system can comprise a high pressure polymerization reactor, e.g., can comprise a tubular reactor and/or an autoclave reactor. Tubular reactors can have several zones where fresh monomer, initiators, or catalysts are added. Monomer can be entrained in an inert gaseous stream and introduced at one zone of the reactor. Initiators, catalysts, and/or catalyst components can be entrained in a gaseous stream and introduced at another zone of the reactor. The gas streams can be intermixed for polymerization. Heat and pressure can be employed appropriately to obtain optimal polymerization reaction conditions.

According to yet another aspect, the polymerization reactor system can comprise a solution polymerization reactor wherein the monomer/comonomer are contacted with the catalyst composition by suitable stirring or other means. A carrier comprising an inert organic diluent or excess monomer can be employed. If desired, the monomer/comonomer can be brought in the vapor phase into contact with the catalytic reaction product, in the presence or absence of liquid material. The polymerization zone can be maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

The polymerization reactor system can further comprise any combination of at least one raw material feed system, at least one feed system for catalyst or catalyst components, and/or at least one polymer recovery system. Suitable reactor systems can further comprise systems for feedstock purification, catalyst storage and preparation, extrusion, reactor cooling, polymer recovery, fractionation, recycle, storage, loadout, laboratory analysis, and process control.

Polymerization conditions that can be controlled for efficiency and to provide desired polymer properties can include temperature, pressure, and the concentrations of various reactants. Polymerization temperature can affect catalyst productivity, polymer molecular weight, and molecular weight distribution. A suitable polymerization temperature can be any temperature below the de-polymerization temperature according to the Gibbs Free energy equation. Typically, the polymerization temperature is in a range from about 35° C. to about 280° C., for example, or from about 50° C. to about 175° C., depending upon the type of polymerization reactor(s). In some reactor systems, the polymerization temperature generally can fall within a range from about 60° C. to about 120° C., or from about 70° C. to about 100° C. Various polymerization conditions can be held substantially constant, for example, for the production of a particular grade of olefin polymer.

Suitable pressures will also vary according to the reactor and polymerization type. The pressure for liquid phase polymerizations in a loop reactor is typically less than 1000 psig (6.9 MPa). The pressure for gas phase polymerization is usually at about 200 to 500 psig (1.4 MPa to 3.4 MPa). High pressure polymerization in tubular or autoclave reactors is generally conducted at about 20,000 to 75,000 psig (138 to 517 MPa). Polymerization reactors can also be operated in a supercritical region occurring at generally higher temperatures and pressures (for instance, above 92° C. and 700 psig (4.83 MPa)). Operation above the critical point of a pressure/temperature diagram (supercritical phase) can offer advantages to the polymerization reaction process.

Also encompassed herein are olefin polymerization processes utilizing any of the catalyst compositions described herein. One such process can comprise contacting a catalyst composition with an olefin monomer and optionally an olefin comonomer in a polymerization reactor system under polymerization conditions to produce an olefin polymer. Generally, the polymerization process can utilize any olefin monomer and optional comonomer disclosed herein, and the catalyst composition employed can be a single (or dual) metallocene catalyst system utilizing, for instance, any of the metallocene compounds, any of activators, and any of the co-catalysts disclosed herein, and the catalyst system can be prepared by any of the processes disclosed herein.

This invention is also directed to, and encompasses, the polymers produced by any of the polymerization processes disclosed herein. Articles of manufacture can be formed from, and/or can comprise, the polymers (e.g., ethylene copolymers) of this invention and, accordingly, are encompassed herein. For example, articles that can comprise polymers of this invention include, but are not limited to, an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, a toy, and the like. Various processes can be employed to form these articles. Non-limiting examples of these processes include injection molding, blow molding, rotational molding, film extrusion, sheet extrusion, profile extrusion, thermoforming, and the like. Additionally, additives and modifiers are often added to these polymers in order to provide beneficial polymer processing or end-use product attributes. Such processes and materials are described in *Modern Plastics Encyclopedia*, Mid-November 1995 Issue, Vol. 72, No. 12; and *Film Extrusion Manual—Process, Materials, Properties*, TAPPI Press, 1992; the disclosures of which are incorporated herein by reference in their entirety.

Also contemplated herein is a method for forming or preparing an article of manufacture comprising a polymer produced by any of the polymerization processes disclosed herein. For instance, a method can comprise (i) contacting any catalyst composition disclosed herein with an olefin monomer and an optional olefin comonomer under polymerization conditions in a polymerization reactor system to produce an olefin polymer (the catalyst composition can be prepared in accordance with any process disclosed herein); and (ii) forming an article of manufacture comprising the olefin polymer. The forming step can comprise blending, melt processing, extruding, molding, or thermoforming, and the like, including combinations thereof.

EXAMPLES

Aspects of the invention are further illustrated by the following examples, which are not to be construed in any way as imposing limitations to the scope of the invention described herein. Various other aspects, modifications, and equivalents thereof which, after reading the description herein, can suggest themselves to one of ordinary skill in the art without departing from the spirit of the present invention or the scope of the appended claims.

Sulfated alumina activator-supports were prepared as follows. Bohemite was obtained from W.R. Grace & Company under the designation "Alumina A" and having a surface area of 300 m$^2$/g, a pore volume of 1.3 mL/g, and an average particle size of 100 microns. This material was impregnated to incipient wetness with an aqueous solution of ammonium sulfate to equal 15 wt. % sulfate. The pore filling or "incipient wetness" impregnation technique used is a method in which the solution is mixed with the dry support until the pores are filled. The definition of the end point of this method can vary somewhat from laboratory to laboratory so that an impregnated catalyst could have a completely dry appearance or a sticky snow-like appearance. However, there is no free-flowing liquid present when the incipient wetness method is employed. The impregnated material was then placed in a flat pan and allowed to dry under vacuum at 110° C. for 16 hr. To calcine the resultant powdered mixture, the material was fluidized in a stream of dry air at 550° C. for 6 hr. Afterward, the sulfated alumina was collected and stored under dry nitrogen, and was used without exposure to the atmosphere.

Fluorided silica-coated alumina activator-supports were prepared as follows. Alumina A was first calcined in dry air at 600° C. for 6 hr, cooled to ambient temperature, and then contacted with tetraethylorthosilicate in isopropanol to equal 25 wt. % SiO$_2$. After drying, the silica-coated alumina was calcined at 600° C. for 3 hr. Fluorided silica-coated alumina (7 wt. % F) was prepared by impregnating the calcined silica-coated alumina with an ammonium bifluoride solution in methanol, drying, and then calcining for 3 hr at 600° C. in dry air. Afterward, the fluorided silica-coated alumina was collected and stored under dry nitrogen, and was used without exposure to the atmosphere.

Polymerization experiments were performed as follows. First, 0.4 mmol of triisobutylaluminum (TIBA, 0.4 mL of a 1M solution in heptane) were added to an autoclave reactor while venting isobutane vapor. Next, approximately 100 mg of fluorided silica-coated alumina (sulfated alumina was used for Example 1) were added to the reactor, followed by a metallocene solution containing 1 mg (2 mg were used for Example 1) of metallocene M1 in toluene. The reactor contents were mixed, the charge port was closed, and 2 L of isobutane were added to the reactor. The contents of the reactor were stirred and heated to the desired polymerization reaction temperature of 90° C., and ethylene was then introduced into the reactor (no hydrogen or comonomer was used). Ethylene was fed on demand to maintain the target pressure of 390 psig pressure for the 30 min length of each polymerization experiment. The reactor was maintained at the desired reaction temperature throughout the experiment by an automated heating-cooling system.

The chemical structure for metallocene M1 is provided below (t-Bu=tert-butyl; Me=methyl):

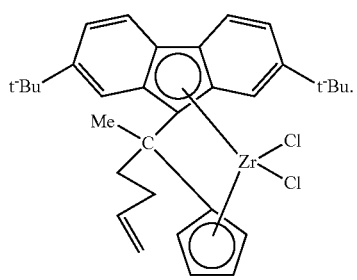

Examples 1-7

Table I summarizes Examples 1-7. In Comparative Examples 1-4, approximately 10-20 mg of solid M1 were placed in a flask, and exposed to air at 25-30° C. for 4-24 hr at 45% relative humidity (Examples 1-3) or for 13 hr at 80% relative humidity (Example 4). Then, toluene was added to the flask to dissolve the exposed solid M1 at a 1 mg/mL concentration. A sample of the M1 solution in toluene was tested immediately (shelf time of "zero" hr) for catalyst activity (amount of solid PE product produced in 30 min) using the standard polymerization procedure described above, while the remaining solution in the flask was stored under nitrogen at 25-30° C. for the respective shelf times indicated in Table I. After storage for 24-26 hr, the catalyst activity of the exposed metallocenes in Examples 1-4 decreased significantly, where at least 65% to over 90% of the catalyst activity was lost due to air exposure of the M1 solid, and storage in a toluene solution for 1 day. Additionally, a visible color change of the solution was noted, from an initial yellow/brown color to a light or pale yellow color. Solutions of the exposed metallocene were unstable, had a short shelf-life, and resulted in poor catalyst activity (i.e., the exposed metallocenes were unusable).

Examples 5-7 were conducted in the same manner as Comparative Examples 1-4, with the respective exposure conditions (13-19 hr, 45%-80% relative humidity) shown in Table I. After exposure, however, the solid M1 in the flask was purged with nitrogen at 25-30° C. for the time period in Table I prior to the addition of toluene to the flask (1 mg of M1 per mL of toluene) and storage under nitrogen for the respective shelf times indicated in Table I. The standard polymerization procedure described above was used to test solutions of M1 at the indicated shelf times. Unexpectedly, after storage of the toluene solution at 25-30° C. for 24-48 hr, no visible color change was noted, and the catalyst activity was effectively unchanged; on average, there was a difference in catalyst activity of less than 10%. Solutions of the treated metallocene were stable, had a long shelf-life, and resulted in excellent catalyst activity (i.e., comparable to the fresh metallocene).

Examples 8-13

Example 8 was a control experiment, in which the solid M1 was stored in a flask under nitrogen, with no exposure to air, prior to addition of toluene to the flask (1 mg M1 per mL toluene). Consequently, catalyst activity was relatively stable over a period of 24-72 hr. Comparative Example 9 was conducted in the same manner as Comparative Examples 1-4, with the respective exposure conditions, shelf times, and catalyst activity shown in Table II. Similar to Comparative Examples 1-4, after storage of the toluene solution at 25-30° C. for 26 hr, the catalyst activity was a fraction of the initial catalyst activity: over 90% of the catalyst activity was lost due to air exposure of the M1 solid, and storage in a toluene solution for 1 day. The solution of the exposed metallocene was unstable, had a short shelf-life, and resulted in poor catalyst activity (i.e., the exposed metallocene was unusable).

In Examples 10-13, solid M1 was exposed to air at 25-30° C. for 8-72 hr at 80% relative humidity in the flask, followed by the nitrogen purging cycles (at 25-30° C.) and vacuum cycles (pressure of 0.5 torr) indicated in Table II, prior to the addition of toluene to the flask (1 mg M1 per mL toluene) and storage under nitrogen for the respective shelf times indicated in Table II. The standard polymerization procedure described above was used to test solutions of M1 at the indicated shelf times. Unexpectedly, after storage of the toluene solution at 25-30° C. for 24-72 hr, the catalyst activity was effectively unchanged. Solutions of the treated metallocene were stable, had a long shelf-life, and resulted in excellent catalyst activity (i.e., comparable to the fresh metallocene).

For solid metallocenes exposed to high moisture conditions for long periods of time, it was noted that nitrogen purging alone may not completely restore catalyst activity, shelf-life, and stability, and that a combination of purging and vacuum treatment may provide superior results.

TABLE I

Examples 1-7.

| Example | Type | M1 exposed to air | Treatment of exposed M1 | Shelf time (hr) | Solid PE (g) |
|---|---|---|---|---|---|
| 1 | Comparative | 19 hr at ~45% humidity | No | 0 | 142 |
|   |   |   |   | 24 | 3 |
| 2 | Comparative | 4 hr at ~45% humidity | No | 0 | 332 |
|   |   |   |   | 24 | 110 |
| 3 | Comparative | 24 hr at ~45% humidity | No | 0 | 320 |
|   |   |   |   | 2 | 193 |
|   |   |   |   | 26 | 15 |
| 4 | Comparative | 13 hr at ~80% humidity | No | 0 | 315 |
|   |   |   |   | 4 | 215 |
|   |   |   |   | 24 | 24 |
| 5 | Inventive | 19 hr at ~45% humidity | Purged M1 with nitrogen for 2 days | 2 | 415 |
|   |   |   |   | 26 | 395 |
| 6 | Inventive | 13 hr at ~45% humidity | Purged M1 with nitrogen for 6 hr | 0 | 368 |
|   |   |   |   | 27 | 413 |
|   |   |   |   | 48 | 349 |

TABLE I-continued

Examples 1-7.

| Example | Type | M1 exposed to air | Treatment of exposed M1 | Shelf time (hr) | Solid PE (g) |
|---|---|---|---|---|---|
| 7 | Inventive | 13 hr at ~80% humidity | Purged M1 with nitrogen for 8 hr | 0 | 354 |
|   |   |   |   | 24 | 291 |

TABLE II

Examples 8-13.

| Example | Type | M1 exposed to air | Treatment of exposed M1 | Shelf time (hr) | Solid PE (g) |
|---|---|---|---|---|---|
| 8 | Control | No | No | 0 | 266 |
|   |   |   |   | 24 | 248 |
|   |   |   |   | 48 | 234 |
|   |   |   |   | 72 | 216 |
| 9 | Comparative | 8 hr at ~80% humidity | No | 0 | 246 |
|   |   |   |   | 26 | 14 |
| 10 | Inventive | 8 hr at ~80% humidity | Purged M1 with nitrogen for 30 min, then vacuum treated for 30 min. Repeated this process 3 times. Then, vacuum treated for an additional 2 hr. | 0 | 279 |
|   |   |   |   | 24 | 278 |
|   |   |   |   | 48 | 256 |
|   |   |   |   | 72 | 251 |
| 11 | Inventive | 8 hr at ~80% humidity | Purged M1 with nitrogen for 30 min, then vacuum treated for 30 min. Repeated this process 3 times. Then, vacuum treated for an additional 2 hr. | 0 | 227 |
|   |   |   |   | 26 | 227 |
|   |   |   |   | 72 | 225 |
| 12 | Inventive | 24 hr at ~80% humidity | Purged M1 with nitrogen for 30 min, then vacuum treated for 30 min. Repeated this process 3 times. Then, vacuum treated for an additional 2 hr. | 0 | 256 |
|   |   |   |   | 24 | 267 |
|   |   |   |   | 48 | 292 |
|   |   |   |   | 72 | 233 |
| 13 | Inventive | 72 hr at ~80% humidity | Purged M1 with nitrogen for 30 min, then vacuum treated for 30 min. Repeated this process 3 times. Then, vacuum treated for an additional 2 hr. | 0 | 282 |
|   |   |   |   | 24 | 299 |
|   |   |   |   | 48 | 297 |
|   |   |   |   | 72 | 259 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A method for treating an exposed solid metallocene compound, the method comprising:
contacting the exposed solid metallocene compound with a purging gas stream comprising an inert gas to form a treated solid metallocene compound.

Aspect 2. A method for treating an exposed solid metallocene compound, the method comprising, in any order:
contacting the exposed solid metallocene compound with a purging gas stream comprising an inert gas; and
subjecting the exposed solid metallocene compound to a sub-atmospheric pressure;
to form a treated solid metallocene compound.

Aspect 3. The method defined in aspect 1 or 2, wherein the purging gas stream comprises any suitable inert gas, or any inert gas disclosed herein, for example, helium, neon, argon, nitrogen, or any combination thereof.

Aspect 4. The method defined in any one of the preceding aspects, wherein the purging gas stream is substantially free of oxygen-containing compounds, for example, less than 25 ppmw (ppm by weight).

Aspect 5. The method defined in any one of the preceding aspects, wherein the purging gas stream is substantially free of water, for example, less than 25 ppmw.

Aspect 6. The method defined in any one of the preceding aspects, wherein the method is conducted under conditions sufficient to reach at least 80%, at least 85%, or at least 90%, of the catalyst activity of a fresh solid metallocene compound, after 24 hours in a toluene solution, under the same polymerization conditions.

Aspect 7. The method defined in any one of the preceding aspects, wherein the method is conducted under conditions sufficient to maintain the color of a 1 mg/mL solution of the treated solid metallocene compound for at least 24 hours at 25° C.

Aspect 8. The method defined in any one of the preceding aspects, wherein the purging step is conducted at a purging temperature in any purging temperature range disclosed herein, for example, from about 0° C. to about 100° C., from about 10° C. to about 75° C., or from about 15° C. to about 50° C.

Aspect 9. The method defined in any one of the preceding aspects, wherein the purging step is conducted for a time period in any range of purging time periods disclosed herein, for example, from about 30 min to about 48 hours, from about 1 to about 12 hours, from about 30 min to about 3 hours, or from about 1 to about 6 hours.

Aspect 10. The method defined in any one of the preceding aspects, wherein the purging step is conducted for a time period sufficient to reach at least 80%, at least 85%, or at least 90%, of the catalyst activity of a fresh solid metallocene compound, after 24 hours in a toluene solution, under the same polymerization conditions.

Aspect 11. The method defined in any one of the preceding aspects, wherein the purging step is conducted for a time period sufficient to maintain the color of a 1 mg/mL solution of the treated solid metallocene compound for at least 24 hours at 25° C.

Aspect 12. The method defined in any one of the preceding aspects, wherein the purging step comprises fluidizing the exposed solid metallocene compound with the purging gas stream.

Aspect 13. The method defined in any one of aspects 2-12, wherein the sub-atmospheric pressure comprises any suitable sub-atmospheric pressure, or any sub-atmospheric pressure disclosed herein, for example, from about 100 to about 0.01 torr, from about 10 to about 0.1 torr, or from about 1 to about 0.1 torr.

Aspect 14. The method defined in any one of aspects 2-13, wherein the subjecting step is conducted for a time period in any range of vacuum time periods disclosed herein, for example, from about 30 min to about 48 hours, from about 1 to about 12 hours, from about 30 min to about 3 hours, or from about 1 to about 6 hours.

Aspect 15. The method defined in any one of aspects 2-14, wherein the subjecting step is conducted at a vacuum temperature in any vacuum temperature range disclosed herein, for example, from about 0° C. to about 100° C., from about 10° C. to about 75° C., or from about 15° C. to about 50° C.

Aspect 16. The method defined in any one of the preceding aspects, wherein the method comprises any number of contacting (purging) cycles disclosed herein (for example, from 1 to 6, or from 2 to 4), and/or any number of subjecting (vacuum) cycles disclosed herein (for example, from 1 to 6, or from 2 to 4), and performed in any order or sequence.

Aspect 17. The method defined in any one of the preceding aspects, wherein the method does not comprise a recrystallization step.

Aspect 18. The method defined in any one of aspects 1-17, wherein the metallocene compound (exposed, treated, fresh) comprises a bridged metallocene compound, for example, any bridged metallocene compound disclosed herein.

Aspect 19. The method defined in any one of aspects 1-17, wherein the metallocene compound (exposed, treated, fresh) comprises a bridged zirconium based metallocene compound with a fluorenyl group, and with no aryl groups on the bridging group.

Aspect 20. The method defined in any one of aspects 1-17, wherein the metallocene compound (exposed, treated, fresh) comprises a bridged zirconium based metallocene compound with a cyclopentadienyl group and a fluorenyl group, and with no aryl groups on the bridging group.

Aspect 21. The method defined in any one of aspects 1-17, wherein the metallocene compound (exposed, treated, fresh) comprises a bridged zirconium or hafnium based metallocene compound with a fluorenyl group, and an aryl group on the bridging group.

Aspect 22. The method defined in any one of aspects 1-17, wherein the metallocene compound (exposed, treated, fresh) comprises a bridged zirconium or hafnium based metallocene compound with a cyclopentadienyl group and fluorenyl group, and an aryl group on the bridging group.

Aspect 23. The method defined in any one of aspects 1-17, wherein the metallocene compound (exposed, treated, fresh) comprises a bridged zirconium based metallocene compound with a fluorenyl group, and an aryl group on the bridging group.

Aspect 24. The method defined in any one of aspects 1-17, wherein the metallocene compound (exposed, treated, fresh) comprises a bridged hafnium based metallocene compound with a fluorenyl group, and an aryl group on the bridging group.

Aspect 25. The method defined in any one of aspects 21-24, wherein the aryl group is a phenyl group.

Aspect 26. The method defined in any one of aspects 1-17, wherein the metallocene compound (exposed, treated, fresh) comprises a bridged zirconium or hafnium based metallocene compound with a cyclopentadienyl group and a fluorenyl group, and with an alkenyl substituent.

Aspect 27. The method defined in any one of aspects 1-17, wherein the metallocene compound (exposed, treated, fresh) comprises a bridged zirconium or hafnium based metallocene compound with two indenyl groups.

Aspect 28. The method defined in any one of aspects 1-17, wherein the metallocene compound (exposed, treated, fresh) comprises a bridged zirconium based metallocene compound with two indenyl groups.

Aspect 29. The method defined in any one of aspects 27-28, wherein the bridging group contains a silicon atom.

Aspect 30. The method defined in any one of aspects 1-17, wherein the metallocene compound (exposed, treated, fresh) comprises an unbridged metallocene compound, for example, any unbridged metallocene compound disclosed herein.

Aspect 31. The method defined in any one of aspects 1-17, wherein the metallocene compound (exposed, treated, fresh) comprises an unbridged zirconium or hafnium based metallocene compound containing two cyclopentadienyl groups, two indenyl groups, or a cyclopentadienyl and an indenyl group.

Aspect 32. The method defined in any one of aspects 1-17, wherein the metallocene compound (exposed, treated, fresh) comprises an unbridged zirconium based metallocene compound containing two cyclopentadienyl groups, two indenyl groups, or a cyclopentadienyl and an indenyl group.

Aspect 33. The method defined in any one of aspects 1-17, wherein the metallocene compound (exposed, treated, fresh) comprises an unbridged zirconium based homodinuclear metallocene compound.

Aspect 34. The method defined in any one of aspects 1-17, wherein the metallocene compound (exposed, treated, fresh) comprises an unbridged hafnium based homodinuclear metallocene compound.

Aspect 35. The method defined in any one of aspects 1-17, wherein the metallocene compound (exposed, treated, fresh) comprises an unbridged heterodinuclear metallocene compound.

Aspect 36. A treated solid metallocene compound prepared by the method defined in any one of the preceding aspects, wherein a 1 mg/mL solution of the treated solid metallocene compound has a moisture level of less than 10 ppmw.

Aspect 37. A process to produce a catalyst composition, the process comprising contacting, in any order:
(a) the treated solid metallocene compound defined in aspect 36;
(b) an activator; and
(c) optionally, a co-catalyst;
to produce the catalyst composition.

Aspect 38. The process defined in aspect 37, wherein the treated solid metallocene compound is present as a slurry in a diluent.

Aspect 39. The process defined in aspect 37, wherein the treated solid metallocene compound is present as a metallocene solution.

Aspect 40. The process defined in any one of aspects 37-39, wherein the activator comprises an aluminoxane compound.

Aspect 41. The process defined in any one of aspects 37-39, wherein the activator comprises an organoboron or organoborate compound.

Aspect 42. The process defined in any one of aspects 37-39, wherein the activator comprises an ionizing ionic compound.

Aspect 43. The process defined in any one of aspects 37-39, wherein the activator comprises an activator-support comprising a solid oxide treated with an electron-withdrawing anion, for example, comprising any solid oxide treated with any electron-withdrawing anion disclosed herein.

Aspect 44. The process defined in aspect 43, wherein the solid oxide comprises silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and the electron-withdrawing anion comprises sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or any combination thereof.

Aspect 45. The process defined in aspect 43, wherein the activator-support comprises a fluorided solid oxide, a sulfated solid oxide, a phosphated solid oxide, or a combination thereof.

Aspect 46. The process defined in aspects 43, wherein the activator-support comprises fluorided alumina, chlorided alumina, bromided alumina, sulfated alumina, phosphated alumina, fluorided silica-alumina, chlorided silica-alumina, bromided silica-alumina, sulfated silica-alumina, phosphated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or any combination thereof.

Aspect 47. The process defined in aspect 43, wherein the activator-support comprises fluorided alumina, fluorided silica-alumina, fluorided silica-zirconia, fluorided silica-coated alumina, fluorided-chlorided silica-coated alumina, or any combination thereof.

Aspect 48. The process defined in aspect 43, wherein the activator-support comprises sulfated alumina, sulfated silica-alumina, sulfated silica-coated alumina, or any combination thereof.

Aspect 49. The process defined in any one of aspects 37-48, wherein the catalyst composition comprises any suitable co-catalyst, or any co-catalyst disclosed herein.

Aspect 50. The process defined in any one of aspects 37-49, wherein the co-catalyst comprises any organoaluminum compound disclosed herein.

Aspect 51. The process defined in aspect 50, wherein the organoaluminum compound comprises trimethylaluminum, triethylaluminum, tri-n-propylaluminum, tri-n-butyl aluminum, triisobutylaluminum, tri-n-hexylaluminum, tri-n-octylaluminum, diisobutyl aluminum hydride, diethyl aluminum ethoxide, di ethyl aluminum chloride, or any combination thereof.

Aspect 52. A catalyst composition produced by the process defined in any one of aspects 37-51.

Aspect 53. An olefin polymerization process, the process comprising contacting the catalyst composition defined in aspect 52 with an olefin monomer and an optional olefin comonomer in a polymerization reactor system under polymerization conditions to produce an olefin polymer.

Aspect 54. The process defined in aspect 53, wherein the olefin monomer comprises any olefin monomer disclosed herein, for example, any $C_2$-$C_{20}$ olefin.

Aspect 55. The process defined in aspect 53, wherein the olefin monomer and the optional olefin comonomer independently comprise a $C_2$-$C_{20}$ alpha-olefin.

Aspect 56. The process defined in any one of aspects 53-55, wherein the olefin monomer comprises ethylene.

Aspect 57. The process defined in any one of aspects 53-56, wherein the catalyst composition is contacted with ethylene and an olefin comonomer comprising a $C_3$-$C_{10}$ alpha-olefin.

Aspect 58. The process defined in any one of aspects 53-57, wherein the catalyst composition is contacted with ethylene and an olefin comonomer comprising 1-butene, 1-hexene, 1-octene, or a mixture thereof.

Aspect 59. The process defined in any one of aspects 53-55, wherein the olefin monomer comprises propylene.

Aspect 60. The process defined in any one of aspects 53-59, wherein the polymerization reactor system comprises a batch reactor, a slurry reactor, a gas-phase reactor, a solution reactor, a high pressure reactor, a tubular reactor, an autoclave reactor, or a combination thereof.

Aspect 61. The process defined in any one of aspects 53-60, wherein the polymerization reactor system comprises a slurry reactor, a gas-phase reactor, a solution reactor, or a combination thereof.

Aspect 62. The process defined in any one of aspects 53-61, wherein the polymerization reactor system comprises a loop slurry reactor.

Aspect 63. The process defined in any one of aspects 53-62, wherein the polymerization reactor system comprises a single reactor.

Aspect 64. The process defined in any one of aspects 53-62, wherein the polymerization reactor system comprises 2 reactors.

Aspect 65. The process defined in any one of aspects 53-62, wherein the polymerization reactor system comprises more than 2 reactors.

Aspect 66. The process defined in any one of aspects 53-65, wherein the olefin polymer comprises any olefin polymer disclosed herein.

Aspect 67. The process defined in any one of aspects 53-58 or 60-66, wherein the olefin polymer comprises an ethylene homopolymer, an ethylene/1-butene copolymer, an ethylene/1-hexene copolymer, or an ethylene/1-octene copolymer.

Aspect 68. The process defined in any one of aspects 53-58 or 60-66, wherein the olefin polymer comprises an ethylene/1-hexene copolymer.

Aspect 69. The process defined in any one of aspects 59-66, wherein the olefin polymer comprises a polypropylene homopolymer or a propylene-based copolymer.

We claim:

1. A method for treating an exposed solid metallocene compound, the method comprising, in any order:
    contacting the exposed solid metallocene compound with a purging gas stream comprising an inert gas; and
    subjecting the exposed solid metallocene compound to a sub-atmospheric pressure;
    to form a treated solid metallocene compound.

2. The method of claim 1, wherein subjecting the exposed solid metallocene compound to a sub-atmospheric pressure comprises:
    a pressure in a range from about 100 torr to about 0.01 torr; and
    a temperature in a range from about 10° C. to about 75° C.

3. The method of claim 1, wherein the method comprises at least two contacting steps and at least two subjecting steps, performed in any order.

4. The method of claim 1, wherein a 1 mg/mL solution of the treated solid metallocene compound in toluene has a moisture content of less than 10 ppmw.

5. The method of claim 1, wherein a color of a 1 mg/mL solution of the treated solid metallocene compound in toluene is unchanged for a time period of 24 hours at 25° C.

6. The method of claim 1, wherein a catalyst activity of a 1 mg/mL solution of the treated solid metallocene compound in toluene is at least 85% of the catalyst activity obtained by using a 1 mg/mL solution of a fresh solid metallocene compound in toluene, after a time period of 24 hours at 25° C., under the same catalyst preparation and polymerization conditions.

7. A method for treating an exposed solid metallocene compound, the method comprising:
    contacting the exposed solid metallocene compound with a purging gas stream comprising an inert gas to form a treated solid metallocene compound.

8. The method of claim 7, wherein:
    the inert gas comprises nitrogen;
    the purging gas stream comprises less than 25 ppmw of water; and
    the purging gas stream comprises less than 25 ppmw of oxygen-containing compounds.

9. The method of claim 7, wherein the method does not comprise a recrystallization step.

10. The method of claim 7, wherein the treated solid metallocene compound comprises an unbridged zirconium or hafnium based metallocene compound containing two cyclopentadienyl groups, two indenyl groups, or a cyclopentadienyl and an indenyl group.

11. The method of claim 7, wherein:
    a 1 mg/mL solution of the treated solid metallocene compound in toluene has a moisture content of less than 5 ppmw;
    a color of a 1 mg/mL solution of the treated solid metallocene compound in toluene is unchanged for a time period of 36 hours at 25° C.; and
    a catalyst activity of a 1 mg/mL solution of the treated solid metallocene compound in toluene is at least 80% of the catalyst activity obtained by using a 1 mg/mL solution of a fresh solid metallocene compound in toluene, after a time period of 24 hours at 25° C., under the same catalyst preparation and polymerization conditions.

12. The method of claim 1, wherein:
    the treated solid metallocene compound comprises titanium, zirconium, hafnium, or a combination thereof; and
    the method does not comprise a recrystallization step.

13. The method of claim 12, wherein:
    subjecting the exposed solid metallocene compound to a sub-atmospheric pressure comprises a pressure of less than 10 torr; and
    a 1 mg/mL solution of the treated solid metallocene compound in toluene has a moisture content of less than 5 ppmw.

14. The method of claim 1, wherein the treated solid metallocene compound comprises a bridged zirconium or hafnium based metallocene compound with a cyclopentadienyl group and a fluorenyl group.

15. The method of claim 14, wherein a catalyst activity of a 1 mg/mL solution of the treated solid metallocene compound in toluene is at least 80% of the catalyst activity obtained by using a 1 mg/mL solution of a fresh solid metallocene compound in toluene, after a time period of 24 hours at 25° C., under the same catalyst preparation and polymerization conditions.

16. The method of claim 1, wherein the treated solid metallocene compound comprises an unbridged zirconium or hafnium based metallocene compound containing two cyclopentadienyl groups, two indenyl groups, or a cyclopentadienyl and an indenyl group.

17. The method of claim 16, wherein:
    the purging gas stream is a nitrogen gas stream comprising less than 10 ppmw of water and less than 10 ppmw of oxygen-containing compounds; and
    a catalyst activity of a 1 mg/mL solution of the treated solid metallocene compound in toluene is at least 80% of the catalyst activity obtained by using a 1 mg/mL solution of a fresh solid metallocene compound in toluene, after a time period of 24 hours at 25° C., under the same catalyst preparation and polymerization conditions.

18. The method of claim 7, wherein:
    the method comprises fluidizing the exposed solid metallocene compound with the purging gas stream; and
    the treated solid metallocene compound comprises titanium, zirconium, hafnium, or a combination thereof.

19. The method of claim 7, wherein:
    the treated solid metallocene compound comprises a bridged zirconium or hafnium based metallocene compound with a cyclopentadienyl group and a fluorenyl group; and
    a catalyst activity of a 1 mg/mL solution of the treated solid metallocene compound in toluene is at least 85% of the catalyst activity obtained by using a 1 mg/mL solution of a fresh solid metallocene compound in toluene, after a time period of 24 hours at 25° C., under the same catalyst preparation and polymerization conditions.

20. The method of claim 7, wherein the purging gas stream is a nitrogen gas stream comprising less than 10 ppmw of water and less than 10 ppmw of oxygen-containing compounds.

* * * * *